(12) United States Patent
Varan et al.

(10) Patent No.: US 11,601,706 B2
(45) Date of Patent: Mar. 7, 2023

(54) WEARABLE EYE TRACKING HEADSET APPARATUS AND SYSTEM

(71) Applicant: Smart Science Technology, LLC, Austin, TX (US)

(72) Inventors: Duane Varan, Austin, TX (US); Sean Michael Ragan, Austin, TX (US)

(73) Assignee: Smart Science Technology, LLC, Austin, TX (US)

( * ) Notice: Subject to any disclaimer, the term of this patent is extended or adjusted under 35 U.S.C. 154(b) by 0 days.

(21) Appl. No.: 16/949,722

(22) Filed: Nov. 12, 2020

(65) Prior Publication Data
US 2022/0150567 A1 May 12, 2022

(51) Int. Cl.
*H04N 21/4223* (2011.01)
*A61B 5/00* (2006.01)
*H04R 1/10* (2006.01)
*G06F 3/01* (2006.01)
*G06V 40/18* (2022.01)

(52) U.S. Cl.
CPC ....... *H04N 21/4223* (2013.01); *A61B 5/6803* (2013.01); *A61B 5/6821* (2013.01); *G06F 3/013* (2013.01); *G06V 40/193* (2022.01); *H04R 1/1066* (2013.01)

(58) Field of Classification Search
CPC .............. H04N 21/4223; A61B 5/6803; A61B 5/6821; G06F 3/013; G06K 9/0061; H04R 1/1066
USPC .......................................................... 348/78
See application file for complete search history.

(56) References Cited

U.S. PATENT DOCUMENTS

| | | | |
|---|---|---|---|
| 2010/0079664 A1* | 4/2010 | MacKenzie | H04N 5/247 348/376 |
| 2014/0160248 A1* | 6/2014 | Pomerantz | H04N 5/2258 348/47 |
| 2014/0347794 A1* | 11/2014 | Pombo | G02B 27/0176 361/679.01 |
| 2015/0070470 A1* | 3/2015 | McMurrough | G06K 9/6211 348/46 |
| 2017/0071495 A1* | 3/2017 | Denison | A61B 5/7264 |

* cited by examiner

*Primary Examiner* — Thai Q Tran
*Assistant Examiner* — Nienru Yang
(74) *Attorney, Agent, or Firm* — Lee & Hayes, P.C.

(57) ABSTRACT

A headset system for tracking eye motion, reaction, facial features, and focus of a user. The system may include an inward-facing camera directed at the front of the user's face to capture image data associated with the eye movement, facial expressions, reaction, and focus of the user. The system may also include at least one additional outward-facing camera directed away from the user's face to capture image data of the viewable content of the user.

18 Claims, 8 Drawing Sheets

WEARABLE EYE TRACKING HEADSET APPARATUS AND SYSTEM

BACKGROUND

The ability to track a focus of an individual consuming content via an electronic display device is becoming more and more common as part of natural language and natural motion processing-based systems. Unfortunately, today's eye tracking devices often incorporate or require the user to wear a pair of specialized glasses that obstructs the user's facial features, thereby impairing the ability of the system to accurately track the eye motion, facial expressions, and focus of the user. Additionally, for users that already wear glasses adding the second pair of glasses can be an uncomfortable situation.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
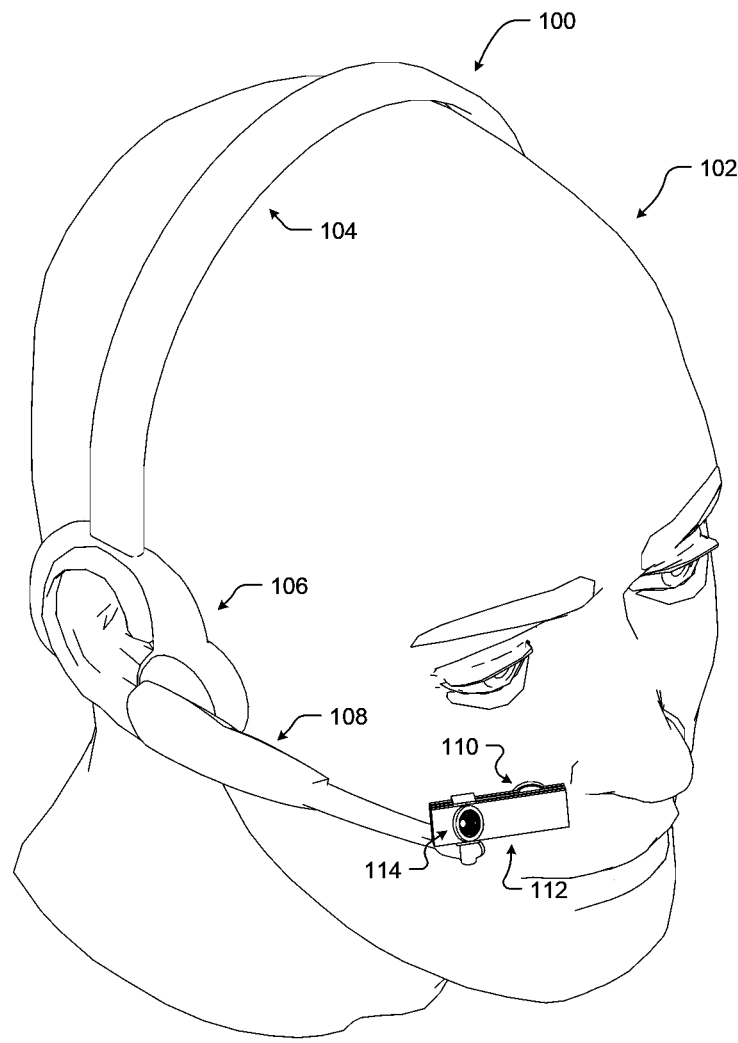
FIG. 1 illustrates an example headset device configured to capture data usable for gaze detection and tracking according to some implementations.

Described herein are devices, systems, and apparatus for tracking eye motion, reaction, facial features, and/or focus of a user. For example, the ability to determine a focus (or portion of a display that a user is consuming or focused on) may assist in refining the layout of user interface design and improving responsiveness and accuracy of natural motion-based input systems. For example, an eye tracking system is described herein that utilizes image data associated with the eyes of the user as well as facial features (such as features controlled by the user's corrugator and/or zygomaticus muscles) to determine a portion of a display that is currently the focus of the user's attention. By utilizing both the eye position (e.g., pupil, iris, corneal reflections, etc.) and the facial features, a more accurate determination of the user's focus can be made (e.g., a smaller portion of the display may be isolated as the user's focus). Additionally, utilizing facial features in conjunction with the focus of the user may allow for determination of the user's mood or reception as the user's mood associates with the particular content displayed on the portion of the display. For example, the system may be configured to determine a word, set of words, image, icon, and the like that is the focus of the user and determine the user's mood as the user views the particular word, set of words, image, icon, and the like. In this manner, the user's response to the content displayed on the particular portion of the display may be determined.

In one example, a headset system may be configured as a wearable appliance that secures one or more inward-facing image capture devices (such as a camera). The inward-facing image capture devices may be secured in a manner that the image capture devices have a clear view of both the eyes as well as well as the cheek or mouth regions (zygomaticus muscles) and forehead region (corrugator muscles) of the user. For instance, the headset system may secure to the head of the user via one or more earpieces or earcups in proximity to the ears of the user. The earpieces may be physically coupled via an adjustable strap configured to fit over the top of the head of the user and or along the back of the user head.

In some implementations, the inward-facing image capture device may be positioned on a boom arm extending outward from the earpiece. In the binocular example, two boom arms may be used (one on either side of the user's head). In this manner, an image capture device may be coupled or attached to each of the boom arms, such that a first image capture device may be used to record data associated with the left eye and a second image capture device may be used to record data associated with the right eye. In this example, either or both of the boom arms may also be equipped with one or more microphones to capture words spoken by the user. In one particular example, the one or more microphones may be positioned on a third boom arm extending toward the mouth of the user.

In some implementations, the earpieces of the headset device may be equipped with one or more speakers to output and direct sound into the ear canal of the user. The earpieces may also be equipped with one or more microphones, such as an array of microphones to provide noise cancelation features in conjunction with the sound output by the speakers. In other examples, the earpieces may be configured to leave the ear canal of the user unobstructed.

In another implementation, the inward-facing image capture device(s) may be positioned on a boom arm extending from the adjustable head-strap. In this implementation, the inward-facing image capture device(s) may be positioned a threshold distance from the head of the user and above the forehead. For example, the boom arm (either extending from an earpiece or the head-strap) may be adjustable and a headset device and/or a remote system configured to process the data collected by the inward-facing image capture devices, may notify the user (e.g., via an audible or visual signal) when the inward-facing image capture devices is positioned correctly (e.g., greater than the threshold distance from the head and above the forehead). In some cases, the image data captured by the inward-facing image capture devices may be displayed to the user, such that the user (or a second user) may correctly align the image capture devices to capture data associated the eyes, forehead, and cheeks.

In various implementations, the headset device may also be equipped with outward-facing image capture device(s). For example, to assist with gaze tracking, the system may be configured to determine a portion or portions of a display (or actual object, such as when the headset device is used in conjunction with a focus group environment) that the user is viewing. In this example, the outward-facing cameras may be configured or positioned to capture a field of view corresponding to the eyes of the user. In some cases, the outward-facing image capture devices may be positioned on the boom arm associated with either earpiece or the head-strap. For instance, the outward-facing image capture devices may positioned opposite each of the inward-facing image capture devices. In one particular example, the outward-facing image capture devices may be positioned on the boom arm associated with the head-strap and the inward-facing image capture device may be positioned on the boom arms associated with the ear pieces. In this manner, the outward-facing image capture devices may be aligned with the eyes of the user and the inward-facing image capture device may be positioned to capture image data of the eyes (e.g., pupil positions, iris dilations, corneal reflections, etc.), cheeks (e.g., zygomaticus muscles), and forehead (e.g., corrugator muscles) on respective sides of the user's face.

In some examples, in addition to the adjustable boom arms, the headset device may include adjustable image capture device mounts that allow the image capture devices to be rotated and/or tilted (e.g., a roll, pitch, and/or yaw may be independently adjustable for each image capture device). In this implementation, the headset device and/or remote system processing the image data captured by the headset device may notify the user (e.g., via an audible or visual signal) when each image capture device is positioned correctly. For example, the system may cause the image data of each image device to be presented on the display together with an alignment indicator. The alignment indicator may, for example, be an icon that turns from red to green when the image capture device is aligned correctly. In some cases, the system may also cause alignment instructions to be presented on the display, such as "tilt the left inward-facing camera upward," "extend boom arm for the left inward-facing camera," and the like. In one particular example, the headset device may be configured to self or automatically adjust the image capture devices based on the image data captured. In this example, each image capture device may include a motorized adjustment assembly that includes a plurality of parameters set by the system based on the image data. In this way, the image capture devise may adjust in response to changes by the user (e.g., position of the user's hair, glasses, and the like) as well as when different users engage the same headset device.

In some implementations the inward-facing and/or outward-facing image capture device may be monocular. In other implementations, the image capture devices may include multiple image capture devices. In one particular implementations, the inward-facing image capture devices may be configured as binocular or dual set of image capture devices capture devices, such that each of the binocular image capture devices are configured to record data associated with an eye and associated facial features of the user. In various implementations, the inward and/or outward image capture devices may have various sizes and figures of merit, for instance, the image capture devices may include one or more wide screen cameras, red-green-blue cameras, mono-color cameras, three-dimensional cameras, high definition cameras, video cameras, monocular cameras, among other types of cameras.

It should be understood, that as the headset system discussed herein does not include specialized glasses or other over the eye coverings, the headset system is able to determine facial expressions and facial muscle movements (e.g., movements of the zygomaticus muscles and/or corrugator muscles) in an unobstructed manner. Additionally, the headset system discussed herein may be used comfortably by individuals that wear glasses on a day to day basis, thereby improving user comfort and allowing more individuals to enjoy a positive experience when using personal eye tracking systems.

FIG. 1 illustrates an example headset device 100 configured to capture data usable for gaze detection and tracking according to some implementations. In the current example, the headset device 100 is being worn by a user 102 that may be consuming digital content via a display device and/or interacting with a physical object (such as in a focus group environment). In this example, the headset device 100 includes a head-strap 104 that is secured to the head of the user 102 via two earpieces, generally indicated by 106. As illustrated, the earpieces 106 are configured to wrap around the ear of the user 102. In this manner, the ear canal is unobstructed and the user 102 may engage in conversation, such as with a focus group facilitator.

A boom arm 108 extends outward from the earpiece 106. The boom arm 108 may extend past the face of the user 102. In some examples, the boom arm 108 may be extendable, while in other case the boom arm 108 may have a fixed position (e.g., length). In some examples, the boom arm 108 may be between five and eight inches in length or adjustable between five and eight inches in length.

In this example, a monocular inward-facing image capture device 110 may be positioned at the end of the boom arm 108. The inward-facing image capture device 110 may be physically coupled to the boom arm 108 via an adjustable mount 112. The adjustable mount 112 may allow the user 102 and/or another individual (such as the focus group facilitator) to adjust the position of the inward-facing image capture device 110 with respect to the face (e.g., eyes, cheeks, and forehead) of the user 102. In some cases, the boom arm 108 may adjust between four and eight inches from the base at the ear piece 106. In some cases, the adjustable mount 112 may be between half an inch and two inches in length, between half an inch and one inch in width, and less than half an inch in thickness. In another case, the adjustable mount 112 may be between half an inch and one inch in length. The adjustable mount 112 may maintain the inward-facing image capture device 110 at a distance of between two inches and five inches from the face or cheek of the user 102.

In some cases, the adjustable mount 112 may allow for adjusting a roll, pitch, and yaw of the inward-facing image capture device 110, while in other cases the adjustable mount 112 may allow for the adjustment of a swivel and tilt of the inward-facing image capture device 110. As discussed above, the inward-facing image capture device 110 may be adjusted to capture image data of the face of the user 102 including the eyes (e.g., pupil, iris, corneal reflections, etc.), the corrugator muscles, and the zygomaticus muscles.

In the current example, the headset device 100 also includes an outward-facing image capture device 114. The outward-facing image capture device 114 may be utilized to assist with determining a field of view of the user 102. For example, if the user 102 is viewing a physical object, the outward-facing image capture device 204 may be able to capture image data of the object that is usable in conjunction with the image data captured by the inward-facing image capture device 110 to determine a portion of the object or location of the gaze of the user 102. In the current example, the outward-facing image capture device 114 is mounted to the adjustable mount 112 with the inward-facing image capture device 110. However, it should be understood that the outward-facing image capture device 204 may have a separate mount in some implementations and/or be independently adjustable (e.g., position, roll, pitch, and yaw) from the inward-facing image capture device 110.

In the current example, a single image capture device 110 is shown. However, it should be understood, that the image capture device 110 may include multiple image capture devices, such as a pair of red-green-blue (RGB) image capture devices, an infrared image capture device, and the like. In other cases, the inward-facing image capture device 110 may be paired with and the adjustable mount 112 may support an emitter (not shown), such as an infrared emitter, projector, and the like, that may be used to emit a pattern onto the face of the user 102 that may be captured by the inward-facing image capture device 110 and used to determine a state of the corrugator muscles, and the zygomaticus muscles of the user 102. In some cases, the emitter and the inward-facing image capture device 110 may be usable to capture data associated with the face of the user 102 to determine an emotion or a user response to stimulus presented either physical or via a display device.

Figure 2A:
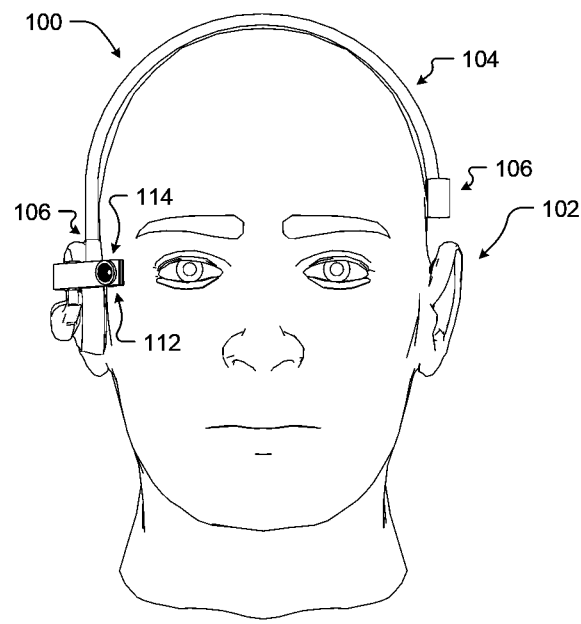
FIG. 2A illustrates a front view of the example headset device of FIG. 1 according to some implementations.
Figure 2B:
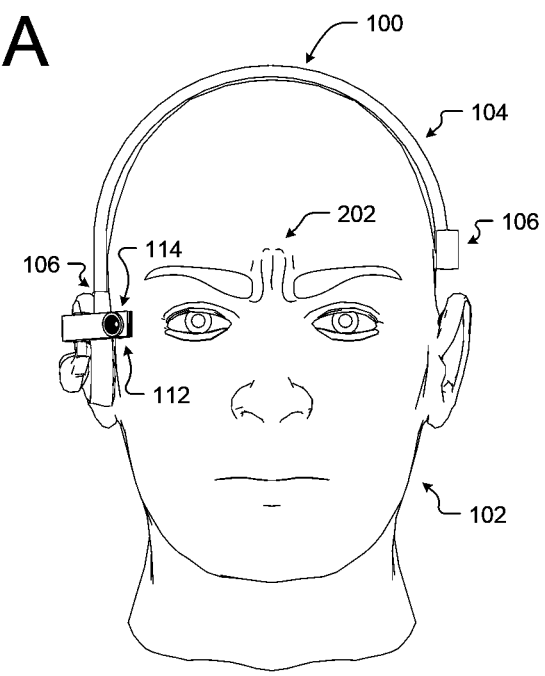
FIG. 2B illustrates another front view of the example headset device of FIG. 1 according to some implementations.

FIGS. 2A and 2B illustrate example front views of the headset device 100 of FIG. 1 according to some implementations. In FIG. 2A, the user 102 may be calm or have little reaction to the stimulus being presented as the headset device 100 captures image data usable to preform gaze tracking. However, in FIG. 2B, the user 102 may be exposed to a stimulus that causes the user 102 to furrow the user's brow (indicating anger, negative emotion, confusion, and/or other emotions) or otherwise contract the corrugator muscles, as indicated by 202. In this example, the inward-facing image capture device 110 may be positioned to capture image data associated with the furrowed brow 202 and the image data may be processed to assist with determining a gaze or focus of the user 102 as well as a mood or emotional response to the stimulus that was introduced.

The headset device 100 also includes the outward-facing image capture device 114. The outward-facing image capture device 114 may be utilized to assist with determining a field of view of the user 102. For example, if the user 102 is viewing a physical object, the outward-facing image capture device 114 may be able to capture image data of the object that is usable in conjunction with the image data captured by the inward-facing image capture device to determine a portion of the object or location of the gaze of the user 102. In the current example, the outward-facing image capture device 114 is mounted to the adjustable mount 112 with the inward-facing image capture device. However, it should be understood that the outward-facing image capture device 114 may have a separate mount in some implementations and/or be independently adjustable (e.g., position, roll, pitch, and yaw) from the inward-facing image capture device 110.

Figure 3A:
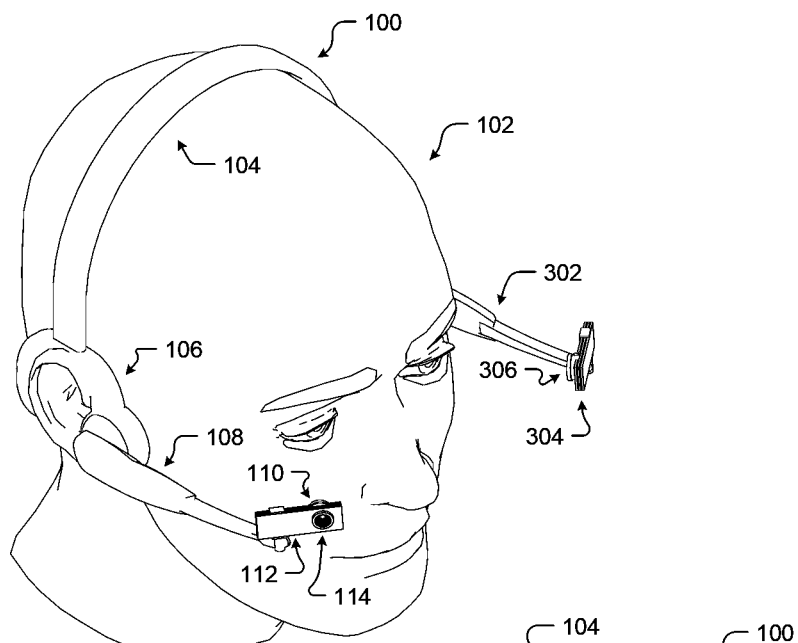
FIG. 3A illustrates an example side view of a headset device of FIG. 1 including a second image capture device for gaze detection and tracking according to some implementations.
Figure 3B:
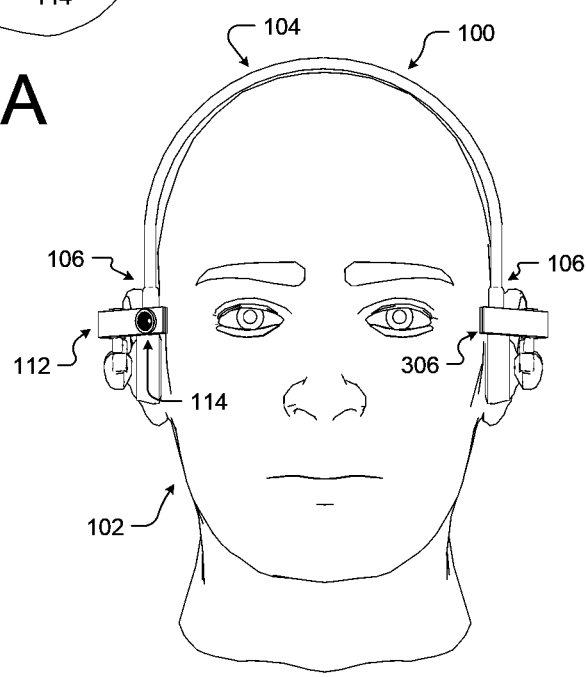
FIG. 3B illustrates an example front view of a headset device of FIG. 1 including a second image capture device for gaze detection and tracking according to some implementations.

FIGS. 3A and 3B illustrate example views of the headset device 100 of FIG. 1 including a second inward-facing image capture device for gaze detection and tracking according to some implementations. In the current example, the headset device 100 is equipped with a second boom arm 302 that is equipped with a second adjustable mount 304. As discussed above, the boom arm 302 may be extendable (e.g., have a variable length) and the adjustable mount 304 may be configured to swivel and tilt (or have adjustable pitch, roll, and yaw) with respect to the boom arm 302.

In the illustrated example, the second inward-facing image capture device 306 further assists with gaze detection and eye tracking of the user 102. For instance, the first inward-facing image capture device 110 may be configured to capture image data associated with the left side of the face of the user 102 and the second inward-facing image capture device 306 may be configured to capture image data associated with the right side of the face of the user 102. In this manner, both eyes, both corrugator muscles, and both zygomaticus muscles may be image captured and the image data maybe usable to assist with gaze detection and eye tracking.

In the examples of FIG. 3, each of the inward-facing image capture devices 110 and 306 are illustrated as a single image capture device. However, it should be understood, that each of the image capture devices 110 and 306 may include multiple image capture devices, such as a RGB image capture device and an infrared image capture device. In other cases, the inward-facing image capture devices 110 and 306 may be paired with an emitter, such as an infrared emitter, projector, and the like, that may be used to emit a pattern onto the corresponding side of the face of the user 102 that may be captured by the inward-facing image capture devices 110 and 306.

In the current illustrated example, the headset device 100 also includes the outward-facing image capture device as discussed above. However, it should be understood that the headset device 100 may also include additional outward-facing image capture devices in a manner similar to the inward-facing image capture devices 110 and 306. For instance, a second outward-facing image capture device may be positioned on the second boom arm 302 and/or along the head-strap 104. In some examples, the headset device 100 may also include three or more inward-facing image capture devices and/or three or more outward-facing image capture devices.

Figure 4A:
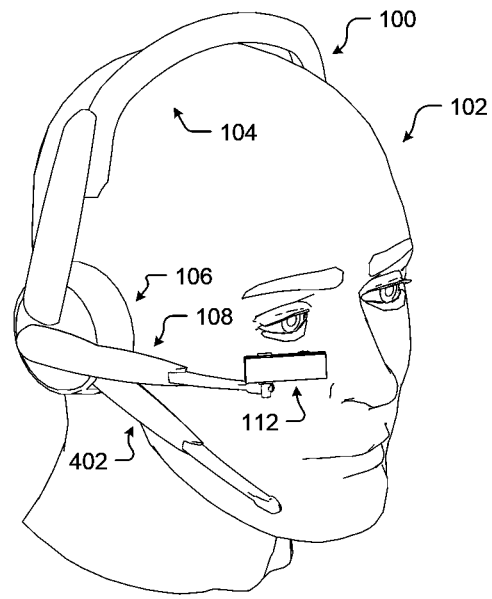
FIG. 4A illustrates an example side view of a headset device of FIG. 1 including a microphone boom arm according to some implementations.
Figure 4B:
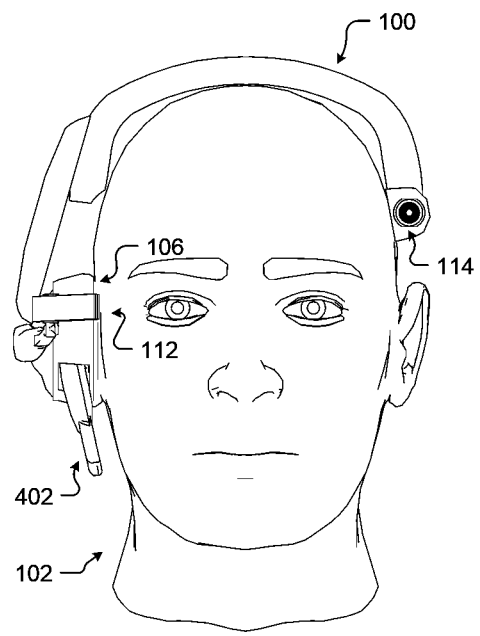
FIG. 4B illustrates an example front view of a headset device of FIG. 1 including a microphone boom arm according to some implementations.

FIGS. 4A and 4B illustrates an example side view of a headset device 100 of FIG. 1 including a microphone boom arm 402 according to some implementations. In this example, the earpiece 106 may be configured to cover or occlude the ear of the user 102, such that audio or sound may be output to the user 102 by one or more speakers within the earpiece 106. In this example, the microphone boom arm 402 may be positioned relative to the mouth of the user 102. The microphone boom arm 402 may be equipped with one or more microphones to capture speech of the user 102. In this example, the user speech may be transmitted to a remote focus group facilitator and the image data captured by the various image capture devices may be transmitted to a remote gaze detection system, as will be discussed in more detail below.

In this example, the outward-facing image capture device 114 is arranged on the headset opposite the adjustable mount 112 containing the inward-facing image capture device. In this arrangement, the outward-facing image capture device 114 may be more easily arranged in a similar line of sight with the eyes of the user. It should be understood, that in other implementations, the outward-facing image capture device 114 may be positioned at other locations on the headset device 100.

Figure 5A:
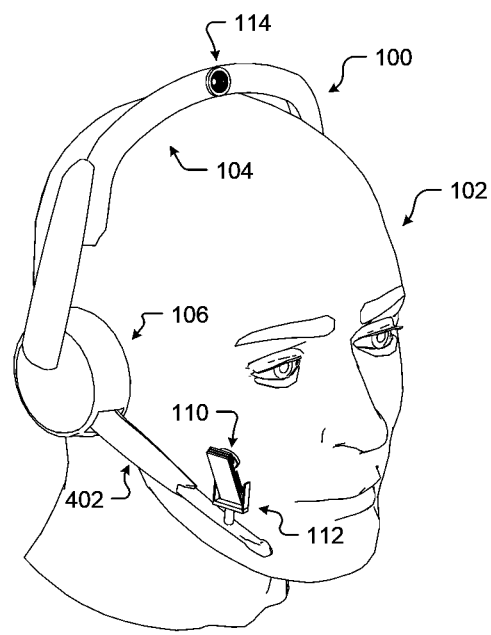
FIG. 5A illustrates an example side view of a headset device of FIG. 1 including the inward-facing image capture device coupled to the microphone boom arm according to some implementations.
Figure 5B:
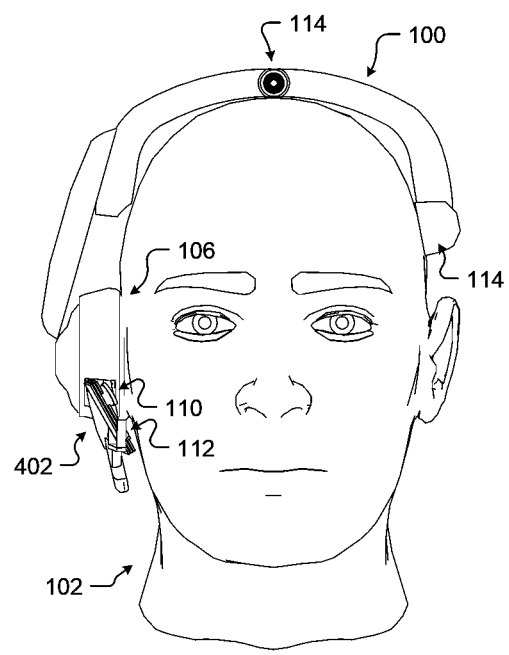
FIG. 5B illustrates an example front view of a headset device of FIG. 1 including the inward-facing image capture device coupled to the microphone boom arm according to some implementations.

FIGS. 5A and 5B illustrate an example side view of a headset device 100 of FIG. 1 including the inward-facing image capture device 110 coupled to the microphone boom arm 402 according to some implementations. In this example, the boom arm 108 may be replaced with the boom arm 402, such that that adjustable mount 112 is coupled in proximity to the end of the boom arm 402. Again, the inward-facing image capture device 110 may be adjustable (e.g., roll, pitch, and yaw) via the adjustable mount 112 and the outward-facing image capture device 114 is arranged along the head-strap 104.

Figure 6A:
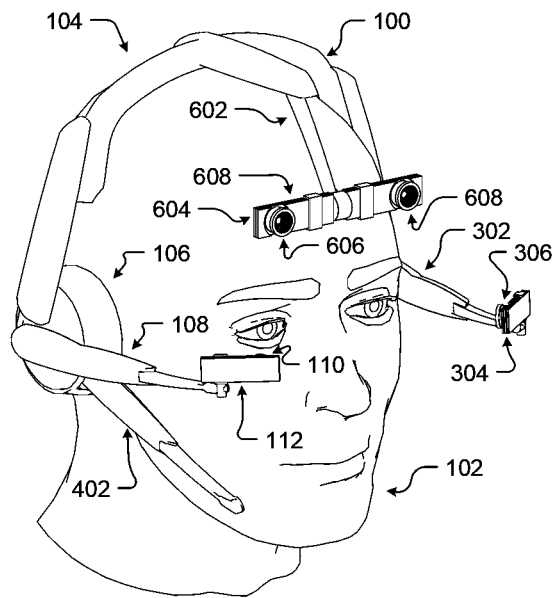
FIG. 6A illustrates an example side view of a headset device of FIG. 1 including an outward-facing image capture mount according to some implementations.
Figure 6B:
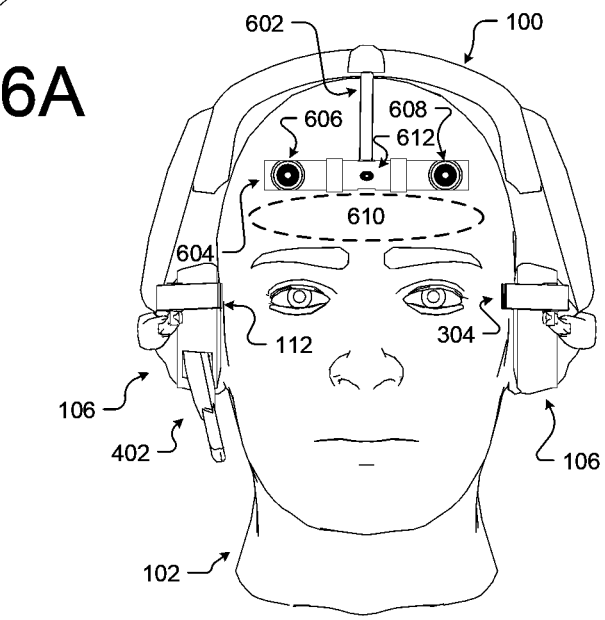
FIG. 6B illustrates an example front view of a headset device of FIG. 1 including the outward-facing image capture mount according to some implementations.

FIGS. 6A and 6B illustrate an example side view of a headset device 100 of FIG. 1 including an outward-facing image capture mount 602 according to some implementations. In the illustrated example, the mount 602 may extend outward from the head-strap 104 and include a horizontal member 604 that includes a left outward-facing image capture device 606 and a right outward-facing image capture device 608. The horizontal member 604 may be positioned above the forehead/eyebrow region, generally indicated by 610, to avoid obstruction a view of the corrugator muscles, as discussed herein. In some cases, the mount 602 may be adjustable in the vertical direction (e.g., up and down the face of the user 102), such that the horizontal member 604 may be adjusted by the user 102 or a focus group facilitator to a correct position above the region 610. In some cases, the horizontal member 604 may between four inches and six inches in width and between a quarter inch and one inch in height.

The image capture devices 606 and 608 may be horizontally movable along the horizontal member 604 via an adjustable mount or slider to allow the outward-facing image capture devices 606 and 608 to align with the respective eyes of the user 102. In this manner, the headset 100 may capture a field of view of the user 102 in a binocular image capture system similar to that experienced by the user 102. The adjustable mount of the horizontal member 604 may be a continuous slide member or have a fixed position to which the image capture devices 606 and 608 may lock or snap. Similar to the inward-facing image capture devices 110 and 402, discussed above, the outward-facing image capture devices 606 and 608 may each include multiple image capture devices, such as a RGB image capture device and an infrared image capture device. In other cases, the outward-facing image capture devices 606 and 608 may be paired with one or more emitters, such as emitter 612, that may be used to emit a pattern onto an object or surface within the field of view of the user 102 to assist with gaze detection and eye tracking.

In some cases, the adjustable mount of the horizontal member 604 as well as the adjustable mounts on the boom arms (such as adjustable mounts 112 and 304) may include a lock mechanism to affix the corresponding image capture devices in place during use and after alignment.

The headset device 100 of FIGS. 6A and 6B includes multiple boom arms 108, 302, 402, and the like and adjustable mounts 112, 306, and the like. It should be understood that the dimensions and distances discussed herein with respect to one of the boom arms 108, 302, 402 or adjustable mounts 112 and 306 may be applicable to each boom arm 108, 302, 402 and each adjustable mount 112 and 306.

FIGS. 1-6B illustrate various examples of the headset 100. It should be understood, that the examples of FIGS. 1-6B are merely for illustration purposes and that components and features shown in one of the examples of FIGS. 1-6B may be utilized in conjunction with components and features of the other examples of FIGS. 1-6B. For instance, the headset 100 may include both the microphone boom arm 402 of FIGS. 4A and 4B and the second inward-facing image capture device 306, the second boom arm 302, and the second adjustable mount 304 of FIGS. 3A and 3B. As another example, the headset 100 may include both the outward-facing image capture device 204 on both the left and right side of the face of the user 102. For instance, the adjustable mount 306 of FIGS. 3A and 3B may include a second outward-facing image capture device as shown on the adjustable mount 112 of FIG. 1. In yet another example, the headset 100 may include the mount 602 of FIGS. 6A and 6B including the outward-facing image capture devices 606 and 608 as well as the outward-facing image capture devices on both the right and left boom arms 112 and 302. Thus, it should be understood that the components and features of the FIGS. 1-6B may be used in conjunction with each other in the same headset device 100 and that the differences between the examples of FIGS. 1-6B are for illustration purposes only.

Figure 7:
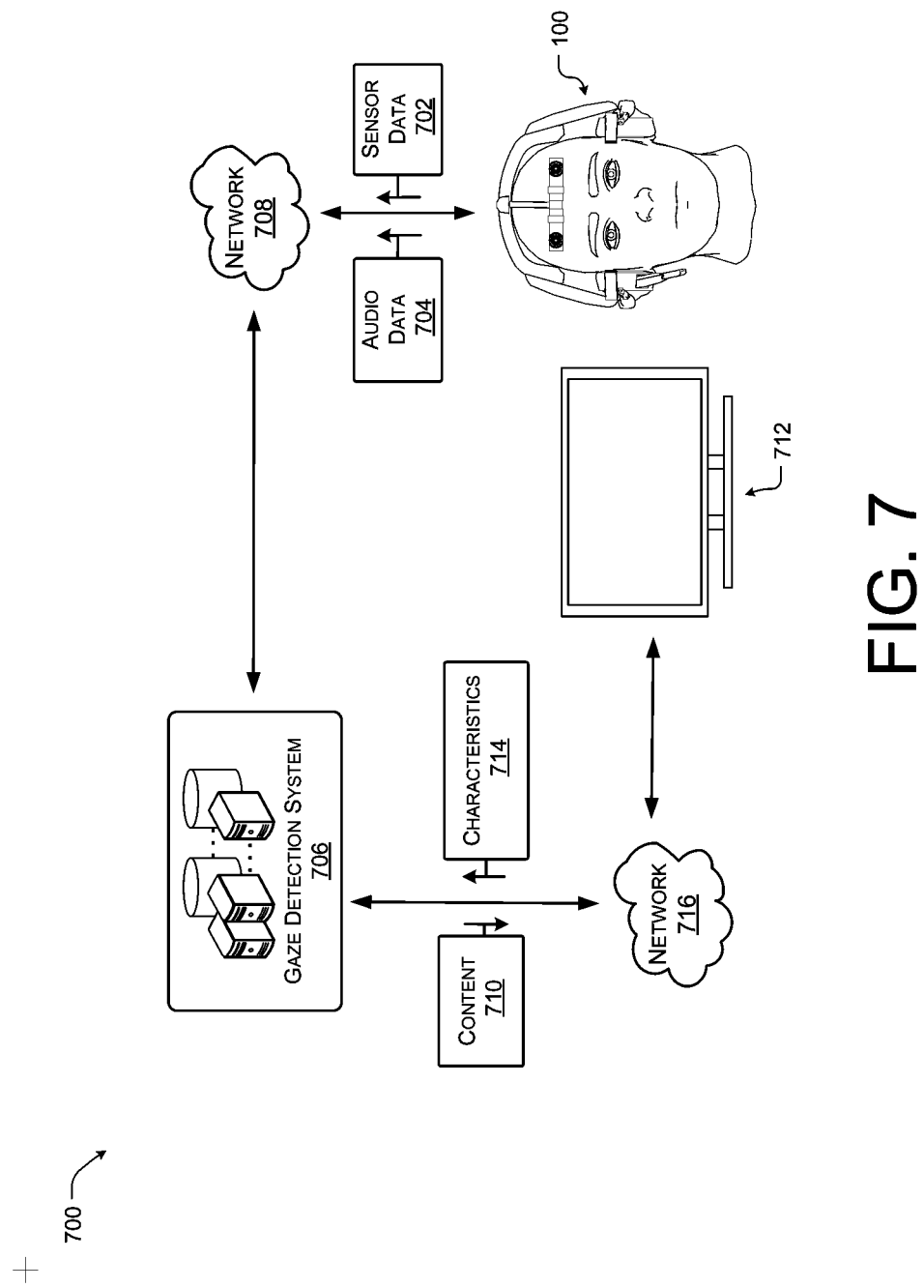
FIG. 7 illustrates an example gaze detection system including the headset device of FIG. 1 according to some implementations.

FIG. 7 illustrates an example gaze detection system including the headset 100 device of FIG. 1 according to some implementations. In the illustrated example, the headset 100 of FIGS. 1-6B, may be configured to capture sensor data 702. The sensor data 702 may include image data captured by the inward-facing image capture devices as well as image data captured by the outward-facing image capture devices. The headset 100 may also capture audio data 704, such as speech of the user that may be provided to a remote operator or focus group facilitator.

In the current example, the sensor data 702 and/or the audio data 704 is sent to a gaze detection system 706 via one or more networks 708. The gaze detection system 706 may also be configured to provide content 710 (e.g., visual content) to a display device 712. In some cases, the display device 712 may also provide characteristics 714 associated with the display, such as screen size, resolution, make, model, type, and the like, to the gaze detection system 706 via one or more networks 716. The gaze detection system 706 may then determine a portion of the content 706 that a user of the headset device 100 is focused on by analyzing the sensor data 702, the characteristics 714, and/or the content 710 provided to the display 712.

Thus, in this example, the gaze detection system 706 may, in addition to, in lieu of, or in combination with the headset device 100, determine a gaze of the user, track eye movement, and/or otherwise determine a focus of the user with respect to the content 710 presented on the display.

Figure 8:
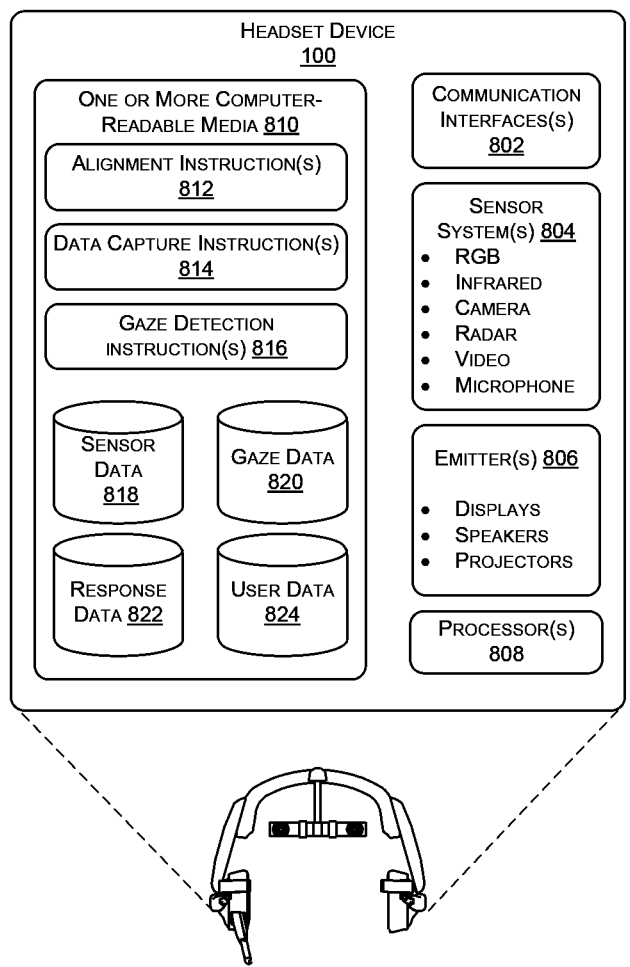
FIG. 8 illustrates an example headset device of FIG. 1 according to some implementations.

FIG. 8 illustrates an example headset device 100 of FIG. 1 according to some implementations. In the illustrated example, the headset device 100 includes one or more communication interfaces 802 configured to facilitate communication between one or more networks, one or more system (e.g., a gaze detection system of FIG. 7). The communication interfaces 802 may also facilitate communication between one or more wireless access points, a master device, and/or one or more other computing devices as part of an ad-hoc or home network system. The communication interfaces 802 may support both wired and wireless connection to various networks, such as cellular networks, radio, WiFi networks, short-range or near-field networks (e.g., Bluetooth®), infrared signals, local area networks, wide area networks, the Internet, and so forth.

In at least some examples, the sensor system(s) 804 may include image capture devices or cameras (e.g., RGB, infrared, monochrome, wide screen, high definition, intensity, depth, etc.), time-of-flight sensors, lidar sensors, radar sensors, sonar sensors, microphones, light sensors, etc. In some examples, the sensor system(s) 804 may include multiple instances of each type of sensors. For instance, multiple inward-facing cameras may be positioned about the headset device 100 to capture image data associated with a face of the user.

The headset device 100 may also include one or more emitter(s) 806 for emitting light and/or sound. The one or more emitter(s) 806, in this example, include interior audio and visual emitters to communicate with the user of the headset device 100. By way of example and not limitation, emitters may include speakers, lights, signs, display screens, touch screens, haptic emitters (e.g., vibration and/or force feedback), and the like. The one or more emitter(s) 804 in this example also includes exterior emitters. By way of example and not limitation, the exterior emitters may include light or visual emitters, such as used in conjunction with the sensors 804 to map or define a surface of an object within an environment of the user as well as one or more audio emitters (e.g., speakers, speaker arrays, horns, etc.) to audibly communicate with, for instance, a focus group.

The headset device 100 includes one or more processors 808, such as at least one or more access components, control logic circuits, central processing units, or processors, as well as one or more computer-readable media 810 to perform the function of the headset device 100. Additionally, each of the processors 808 may itself comprise one or more processors or processing cores.

Depending on the configuration, the computer-readable media 810 may be an example of tangible non-transitory computer storage media and may include volatile and non-volatile memory and/or removable and non-removable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 808.

Several modules such as instructions, data stores, and so forth may be stored within the computer-readable media 810 and configured to execute on the processors 808. For example, as illustrated, the computer-readable media 810 stores alignment instructions 812, data capture instructions 814, and gaze detection instructions 816, as well as other instructions, such as an operating system. The computer-readable media 810 may also be configured to store data, such as sensor data 818 collected or captured with respect to the sensor systems 804, gaze data 820 (e.g., gaze detection data, focus data, and/or eye tracking data determined from the sensor data 818), response data 822 (e.g., as a mood of the user determined from the sensor data 818), and user data 824 (e.g., data associated with various user of the headset device 100).

The alignment instructions 812 may be configured to assist the user with correctly aligning the various components of the headset device 100, such as the inward and outward-facing image capture devices to perform gaze detection and eye tracking. For example, the user may activate the headset device 100 once placed upon the head of the user. The alignment instructions 812 may cause image data being captured by the various inward and outward-facing image capture device to be displayed on a remote display device visible to the user. The alignment instructions 812 may also cause alignment instructions associated with each image capture device to be presented on the remote display.

For example, the alignment instructions 812 may be configured to analyze the image data from each image capture device to determine if it is correctly aligned (e.g., aligned within a threshold or is capturing desired features). In one example, the headset device 100 may include a left inward-facing image capture device and a right inward-facing image capture device. In this example, the alignment instructions 812 may select one of the image capture devices to align first, such as the left inward-facing image capture device. In addition to displaying the image data captured by the image capture device, the alignment instructions 812 may cause a list of features to be displayed. The list of features may include the facial features associated with the left inward-facing image capture device, for instance, the left eye, the left cheek, and the left side of the forehead or eyebrow region. Once each of the left inward-facing image capture devices is aligned to capture each of the features, the alignment instructions 812 may then proceed to assist in aligning the right inward-facing image capture device. Again, the alignment instructions 812 may present the image data captured by the right inward-facing image capture device and a list of associated features to be displayed until each feature is within the field of view of the right inward-facing image capture device.

The alignment instructions 812 may also assist in aligning the outward-facing image capture devices. For example, the alignment instructions 812 may utilize the aligned inward-facing image capture device data to determine if the outward-facing image capture devices are aligned with the eyes of the user. The alignment instructions 812 may then cause alignment instructions to be presented on the remote display, such as "adjust the left outward-facing image capture device to the left" and so forth until each outward-facing image capture device is aligned with the user's field of view.

In some cases, the alignment instructions 812 may also instruct the user to adjust the horizontal member to avoid obstructing the forehead or eyebrow region of the user's face. Also, in addition to the providing visual instructions to a remote display, the alignment instructions 812 may utilize audio instructions output by one or more speakers, as discussed above with respect to FIGS. 4A and 4B.

The data capture instructions 814 may be configured to cause the image capture devices to capture image data associated with the face of the user and/or the environment surrounding the user. The data capture instructions 814 may be configured to time stamp the image data such that the data captured by different image capture devices may be compared using the corresponding time stamps. In some cases, the data capture instructions 814 may cause the communication interfaces 802 to transmit, send, or stream the image data to remote systems for processing.

The gaze detection instructions 816 may be configured to parse or otherwise analyze the sensor data 818 to determine a gaze or focus of the user. For example, the gaze detection instructions 816 may utilize the data from the inward-facing image capture devices and the outward-facing image capture devices to determine a portion of a display that the user is focused on when viewing particular content.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A system comprising:
   a first earpiece and a second earpiece;
   a head-strap coupled between the first earpiece and the second earpiece, the head-strap configured to extend around a head of a user;
   a first boom arm having a first end and a second end, the first end of the first boom arm coupled to the first earpiece and wherein the boom arm extends outward from the first earpiece past a face plane of the user;
   a first adjustable mount coupled in proximity to the second end of the first boom arm, the first adjustable mount to tilt and swivel with respect to the first boom arm;
   a first camera coupled to the first adjustable mount, the first camera facing inward toward the face of the user; and
   a second camera, the second camera coupled to the head-strap above the eyes of the user and facing outward from the face of the user;
   a second boom arm having a first end and a second end, the first end of the second boom arm coupled to the second earpiece and wherein the boom arm extends outward from the second earpiece past the face plane of the user;
   a second adjustable mount coupled in proximity to the second end of the second boom arm, the second adjustable mount to tilt and swivel with respect to the second boom arm; and
   a third camera coupled to the second adjustable mount, the third camera facing inward toward the face of the user, wherein the first camera is configured to capture first image data associated with the left side of the face of the user and the third camera is configured to capture second image data associated with the right side of the face of the user;
   a horizontal member coupled to the head-strap via a mount, the horizontal member positioned over a forehead region of the face of the user; and
   a fourth camera coupled to the horizontal member at a position above a left eye of the user and over a first portion of the forehead region of the user, wherein the second camera is coupled to the horizontal member at a position above a right eye of the user and over a second portion of the forehead region of the user.

2. The system as recited in claim 1, wherein:
   the position of the second camera and the position of the fourth camera with respect to the horizontal member are adjustable; and
   a height of the horizontal member with respect to the forehead of the user is adjustable.

3. The system as recited in claim 1, further comprising at least one emitter coupled to the horizontal member.

4. The system as recited in claim 1, wherein the second camera is positioned relative to the system to capture first image data associated with a field of view of the user.

5. The system as recited in claim 1, wherein the first camera is an infrared camera and further comprising an infrared emitter, the infrared emitter coupled to the adjustable mount and configured to emit infrared light at the face of the user.

6. The system as recited in claim 1, further comprising:
   one or more communication interfaces;
   one or more processors; and
   computer-readable storage media storing computer-executable instructions, which when executed by the one or more processors cause the one or more processors to:
   cause the first camera to capture third image data associated with the eyebrow region of the face of the user, a cheek region of the face of the user, and an eye region of the face of the user;
   determine based at least in part on the first image data and the third image data an area of focus of the user; and
   send, via the one or more communication interfaces, the area of focus to a remote system.

7. The system as recited in claim 1, further comprising:
   a microphone coupled proximate to the second end of the first boom arm; and
   a speaker coupled to the first earpiece and arranged to output audio into an ear canal of the user.

8. A system comprising:
   a first earpiece;
   a head-strap coupled between the first earpiece, the head-strap configured to extend over and secure the system to a head of a user;
   a first boom arm having a first end and a second end, the first end of the first boom arm coupled to the first earpiece and wherein the second end of the boom arm extends outward from the first earpiece past a face plane of the user;
   a first camera coupled in proximity to the second end of the first boom arm, the first camera facing inward toward the face of the user;
   a first adjustable mount having a first surface and a second surface opposite the first surface, the first adjustable mount coupled to the second end of the first boom arm, the first camera coupled to the first surface of the first adjustable mount and the first adjustable mount to adjust a roll, pitch, or yaw of the first camera; and
   a second camera coupled to the second surface of the adjustable mount on the head-strap and facing outward from the face of the user in an opposing direction to the first camera.

9. The system as recited in claim 8, wherein the first adjustable mount includes a first joint and a second joint, the first joint movable independently from the second joint.

10. The system as recited in claim 8, wherein the first camera comprises a red-green-blue camera and an infrared camera.

11. The system as recited in claim 8, further comprising:
   a horizontal member coupled to the head-strap, the horizontal member positioned above a forehead region of the face of the user;
   a third camera coupled to the horizontal member at a position above a left eye of the user; and a fourth camera coupled to the horizontal member at a position above a right eye of the user.

12. The system as recited in claim 8, further comprising:
a second boom arm having a first end and a second end, the first end of the second boom arm coupled to the second earpiece and wherein the boom arm extends outward from the second earpiece past the face plane of the user; and
a second camera coupled in proximity to the second end of the second boom arm, the second camera facing inward toward the face of the user; and
wherein the first camera is configured to capture first image data associated with the left side of the face of the user and the second camera is configured to capture second image data associated with the right side of the face of the user.

13. The system as recited in claim 8, further comprising an infrared emitter coupled proximate to the second end of the first boom arm and configured to emit infrared light at the face of the user.

14. The system as recited in claim 8, further comprising:
one or more communication interfaces;
one or more processors; and
computer-readable storage media storing computer-executable instructions, which when executed by the one or more processors cause the one or more processors to:
cause the first camera to capture first image data associated with a face of the user;
cause the first image data to be presented on a display remote from the system via the one or more communication interfaces;
determine at least one alignment issue based at least in part on the first image data;
cause the adjustment instructions to be presented on the remote display from the system via the one or more communication interfaces, the adjustment instructions to assist the user in aligning the first camera with respect to the face of the user.

15. A head wearable system comprising:
a first earpiece and a second earpiece;
a head-strap coupled between the first earpiece and the second earpiece, the head-strap configured to extend around a head of a user;
a first boom arm having a first end and a second end, the first end of the first boom arm coupled to the first earpiece and wherein the boom arm extends outward from the first earpiece past a face plane of the user;
a second boom arm having a first end and a second end, the first end of the second boom arm coupled to the second earpiece and wherein the boom arm extends outward from the second earpiece past the face plane of the user;
a first adjustable mount coupled in proximity to the second end of the first boom arm, the first adjustable mount to tilt and swivel with respect to the first boom arm;
a second adjustable mount coupled in proximity to the second end of the second boom arm, the second adjustable mount to tilt and swivel with respect to the second boom arm;
a first camera coupled to the first adjustable mount, the first camera facing inward toward the face of the user;
a second camera coupled to the second adjustable mount, the second camera facing inward toward the face of the user, wherein the first camera is configured to capture first image data associated with the left side of the face of the user and the second camera is configured to capture second image data associated with the right side of the face of the user;
a horizontal member coupled to the head-strap via a mount, the horizontal member positioned over a forehead region of the face of the user;
a third camera coupled to the horizontal member at a position above a left eye of the user and over a first portion of the forehead region of the user; and
a fourth camera coupled to the horizontal member at a position above a right eye of the user and over a second portion of the forehead region of the user.

16. The head wearable system as recited in claim 15, further comprising:
a microphone coupled proximate to the second end of the first boom arm; and
a speaker coupled to the first earpiece and arranged to output audio into an ear canal of the user.

17. The head wearable system as recited in claim 15, further comprising:
a third boom arm having a first end and a second end, the first end of the first boom arm coupled to the first earpiece and wherein the boom arm extends outward from the first earpiece below the first boom arm;
a microphone coupled proximate to the second end of the third boom arm; and
a speaker coupled to the first earpiece and arranged to output audio into an ear canal of the user.

18. The head wearable system as recited in claim 15, further comprising:
one or more communication interfaces;
one or more processors; and
computer-readable storage media storing computer-executable instructions, which when executed by the one or more processors cause the one or more processors to:
cause the first camera to capture first image data associated with a left eyebrow region of the face of the user, a left cheek region of the face of the user, and a left eye region of the face of the user;
cause the second camera to capture second image data associated with a right eyebrow region of the face of the user, a right cheek region of the face of the user, and a right eye region of the face of the user;
cause the third camera and the fourth camera to capture third image data associated with a field of view of the user;
determine based at least in part on the first image data, the second image data, and the third image data an area of focus of the user; and
send, via the one or more communication interfaces, the area of focus to a remote system.

* * * * *